United States Patent
Lian (10) Patent No.: US 9,993,191 B2
(45) Date of Patent: Jun. 12, 2018

(54) ONBOARD SYSTEM FOR MITIGATING DISTRACTION RISK

(71) Applicant: THUNDER POWER NEW ENERGY VEHICLE DEVELOPMENT COMPANY LIMITED, Central (HK)

(72) Inventor: Po-Han Lian, Taichung (TW)

(73) Assignee: THUNDER POWER NEW ENERGY VEHICLE DEVELOPMENT COMPANY LIMITED, Central (HK)

( * ) Notice: Subject to any disclaimer, the term of this patent is extended or adjusted under 35 U.S.C. 154(b) by 0 days. days.

(21) Appl. No.: 14/981,966

(22) Filed: Dec. 29, 2015

(65) Prior Publication Data

US 2017/0181684 A1 Jun. 29, 2017

(51) Int. Cl.
*A61B 5/18* (2006.01)
*B60W 40/09* (2012.01)
(Continued)

(52) U.S. Cl.
CPC ............... *A61B 5/18* (2013.01); *A61B 3/113* (2013.01); *A61B 5/0077* (2013.01); *A61B 5/0205* (2013.01); *A61B 5/7282* (2013.01); *B60K 28/06* (2013.01); *B60W 40/09* (2013.01); *A61B 5/024* (2013.01); *B60K 2350/355* (2013.01); *B60K 2350/357* (2013.01); *B60K 2350/901* (2013.01); *B60W 2540/22* (2013.01)

(58) Field of Classification Search
CPC ....... A61B 5/18; A61B 5/0077; A61B 5/0205; A61B 5/7282; A61B 5/024; A61B 3/113; B60K 28/06; B60K 2350/355; B60W 40/09
See application file for complete search history.

(56) References Cited

U.S. PATENT DOCUMENTS

2009/0105953 A1* 4/2009 Sugano ................. B60W 30/16
701/301
2010/0014712 A1* 1/2010 Sampedro Diaz ... G08G 1/0104
382/104
(Continued)

FOREIGN PATENT DOCUMENTS

WO 2016/115053 A1 7/2016

OTHER PUBLICATIONS

European Office Action and Search Report for EP 16202346 dated Sep. 18, 2017, 7 pages.

*Primary Examiner* — Abby Y Lin
(74) *Attorney, Agent, or Firm* — Kilpatrick Townsend & Stockton LLP (57) ABSTRACT

Described herein is an onboard vehicle system capable of determining that a driver of a vehicle is distracted and implementing one or more distraction settings to mitigate unsafe driving conditions. In some embodiments, the onboard vehicle system includes one or more input sensors configured to gather input related to a driver, one or more component adjusters configured to adjust attributes of a vehicle component, and a processor device configured to receive input from the one or more input sensors, determine whether the driver is distracted, and activate the one or more component adjusters. In some embodiments, the onboard vehicle system may be in communication with a service provider computer configured to maintain a user account for a driver along with a driver distraction profile.

14 Claims, 6 Drawing Sheets

(51) Int. Cl.
  *B60K 28/06*   (2006.01)
  *A61B 3/113*   (2006.01)
  *A61B 5/00*    (2006.01)
  *A61B 5/0205*  (2006.01)
  *A61B 5/024*   (2006.01)

(56) References Cited

U.S. PATENT DOCUMENTS

| | | | |
|---|---|---|---|
| 2010/0030434 A1* | 2/2010 | Okabe | A61B 5/165 |
| | | | 701/48 |
| 2011/0246028 A1* | 10/2011 | Lisseman | B60K 28/066 |
| | | | 701/45 |
| 2012/0212353 A1* | 8/2012 | Fung | B60K 28/06 |
| | | | 340/905 |
| 2013/0070043 A1* | 3/2013 | Geva | B60K 28/066 |
| | | | 348/14.02 |
| 2013/0135109 A1* | 5/2013 | Sharon | G08B 21/02 |
| | | | 340/576 |
| 2013/0245886 A1 | 9/2013 | Fung et al. | |
| 2014/0285216 A1* | 9/2014 | Cuddihy | G01R 27/2605 |
| | | | 324/658 |
| 2015/0038123 A1 | 2/2015 | Tuukkanen et al. | |
| 2015/0061875 A1* | 3/2015 | Yang | A61B 5/1071 |
| | | | 340/576 |
| 2015/0191178 A1* | 7/2015 | Roy | B60W 40/09 |
| | | | 701/36 |
| 2015/0314803 A1* | 11/2015 | Kojo | B60T 8/1755 |
| | | | 701/43 |
| 2016/0046298 A1* | 2/2016 | DeRuyck | B60W 40/09 |
| | | | 340/576 |

\* cited by examiner

ONBOARD SYSTEM FOR MITIGATING DISTRACTION RISK

BACKGROUND

Driving while distracted can be hazardous, both for the driver of a vehicle, as well as for other drivers in the vicinity of that vehicle. Ideally, drivers should avoid distractions while driving. However, it is sometimes not possible to avoid every distraction that can catch a driver's attention. Accordingly, it may be advantageous to identify drivers that are distracted. However, not only is it difficult to identify distracted drivers, but even if distracted drivers could be identified, it is difficult to mitigate unsafe driving conditions caused by driver distraction.

SUMMARY

The present disclosure solves these and other problems with the current technology. In particular, the disclosure provides a vehicle's onboard system capable of putting into place distraction settings upon determining that a driver is distracted. In particular, the onboard system includes a steering wheel that is fitted with one or more input sensors capable of detecting that a driver is distracted. Upon making a determination that the driver is distracted, the onboard system may reduce the sensitivity of the vehicle throttle, increase the sensitivity of the vehicle braking system, and/or enact any other suitable distraction setting in order to increase the safety of the driving experience. In another example, a vehicle's ADAS system may be activated upon detecting that the driver is distracted. This may result in an electronic stability program (ESP) taking over control of the braking/steering functions in order to increase the safety of the driving experience.

BRIEF DESCRIPTION OF THE DRAWINGS

Various embodiments in accordance with the present disclosure will be described with reference to the drawings, in which:

FIG. 1 depicts an onboard vehicle distraction detection system utilizing one or more input sensors in accordance with at least some embodiments;

FIG. 4 depicts an illustrative use case involving a driver in accordance with at least some embodiments;

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Described herein is an onboard vehicle system comprising one or more input sensors capable of detecting input related to a driver, a processor device capable of interpreting the detected input, and one or more component adjusters configured to interact with components of the vehicle. Some embodiments may also include a communication means for communicating with a service provider computer (e.g., a wireless network antenna).

In some embodiments, an onboard system may include a processor device that receives input from one or more input sensors. Upon receiving the input from the one or more input sensors, the onboard system may utilize it to determine whether the driver is currently distracted. If the driver is determined to be distracted, then the processor device may take one or more actions to make the driver's driving safer. In some embodiments, the rules needed to determine whether a driver is distracted may be specific to a particular driver. In these embodiments, the onboard system may utilize a distraction profile tailored to the particular driver.

Prior to discussing specific embodiments of the invention, some terms may be described in detail.

An "onboard system" may be any system housed within a vehicle. For example, an onboard system may include a number of input sensors, a processor device capable of processing data from the input sensors, a transmission means (e.g., a wireless platform), and any other suitable component. In some embodiments, the onboard system may be in communication with one or more component external to the onboard system.

A "component adjuster" may be any device configured to interact with a component of a vehicle. In some embodiments, a component adjuster may be an electronic switch configured to adjust the effectiveness of a vehicle component. For example, a component adjuster may be integrated into the master cylinder component of the vehicle's braking system. In this example, the component adjuster may be used to adjust the sensitivity of the braking system (e.g., by adjusting hydraulic pressure within the system). In some embodiments, a component adjuster may activate an advanced driver assistance system (ADAS). For example, the component adjuster may activate lighting, activate adaptive cruise control, activate automatic braking, activate incorporated GPS/traffic warnings, activate functionality to keep the driver in the correct lane, and/or activate a blind spot monitor. In some embodiments, multiple component adjusters may be utilized in a single onboard system. For example, a first component adjuster may increase brake sensitivity and a second component adjuster may decrease throttle sensitivity.

A "distraction profile" may be any set of indicators specific to a particular driver or vehicle that may be useful in determining whether the driver is distracted. For example, if a particular driver has a habit of texting while driving, then a distraction profile may include an indicator such that if the driver removes one hand from the steering wheel, the onboard system may determine that the driver is distracted. In another example, a distraction profile may include an indication that a particular driver's heartrate tends to be higher than average. This may prevent the onboard system from determining that the driver is distracted based on an elevated heart rate. In some embodiments, a distraction profile may be stored at a service provider computer and loaded into memory of the vehicle by the service provider. In some embodiments, the distraction profile may be created by a processor device of the onboard system within a vehicle based on one or more actions taken by the driver of the vehicle.

"Distraction settings" are any vehicle configuration settings, that, when applied to components within the vehicle, are intended to make driving of the vehicle safer for a distracted driver. For example, enabling distraction settings may result in an increased sensitivity of the vehicle braking system and/or a decreased sensitivity of the vehicle throttle system. In some embodiments, distraction settings may be unique to a particular driver. In some embodiments, a set of distraction settings may be provided to a vehicle by a service provider computer.

A "vehicle component" may be any device capable of executing at least one function of a vehicle. For example, a master cylinder is a vehicle component that executes a vehicle's braking function by applying hydraulic pressure to a brake disk. In some embodiments, the master cylinder may be signaled to execute the vehicle's brakes by a processor device. In some embodiments, the hydraulic pressure of the braking system may be increased at the master cylinder in order to increase the amount of braking force applied to the brake disk in response to an amount of movement of the brake pedal.

Figure 1A:
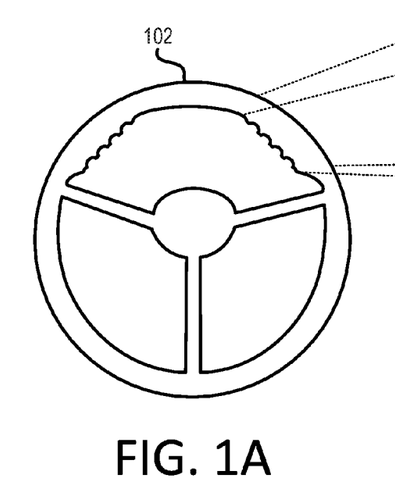
FIG. 1A depicts a depiction of a steering wheel in accordance with at least some embodiments.
Figure 1B:
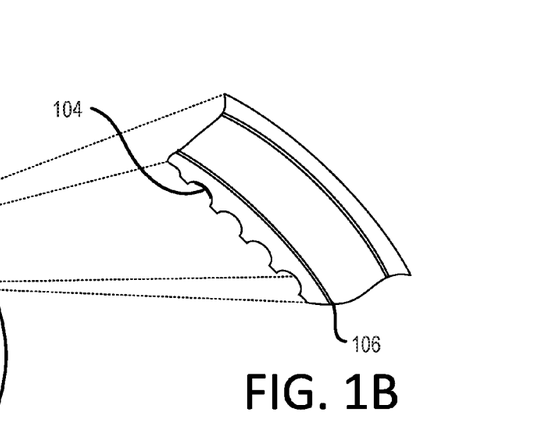
FIG. 1B depicts a first cross-sectional view of the steering wheel in accordance with at least some embodiments.
Figure 1C:
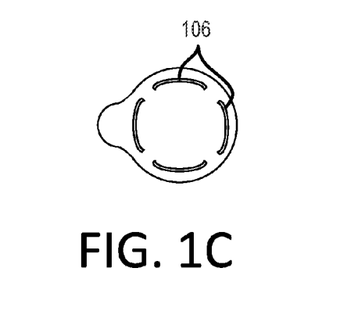
FIG. 1C depicts a second cross-sectional view of the steering wheel in accordance with at least some embodiments.

FIG. 1 depicts an onboard vehicle distraction detection system utilizing one or more input sensors in accordance with at least some embodiments. In FIG. 1, a steering wheel 102 is depicted as including multiple input sensors capable of detecting input related to a driver. In order to better illustrate some aspects of the described system, FIG. 1 is broken into FIG. 1A (a depiction of a steering wheel), FIG. 1B (a first cross-sectional view of the steering wheel), and FIG. 1C (a second cross-sectional view of the steering wheel).

In some embodiments, the steering wheel may include input sensors capable of detecting a driver's biometric information. For example, the steering wheel may include a heart rate sensor 104 capable of detecting a driver's heart rate. The onboard system may be configured to determine, using information collected from the heart rate sensor 104, that a user is distracted. For example, the heart rate sensor may be utilized to identify a baseline heartrate for a particular driver. Upon detecting that the current heartrate is above the baseline heartrate, the onboard system may determine that the driver is stressed out, scared, or otherwise distracted. In another example, the input sensor may include a thermometer, sweat sensor, or any other input sensor capable of detecting a driver's biometric data. In some embodiments, the onboard system may include a camera device capable of capturing a driver's facial expressions. The driver's facial expressions may be interpreted using one or more image processing techniques and may be used to identify a state of mind for the driver. In some embodiments, the onboard system may include eye-tracking cameras capable of tracking a driver's eye movements. The onboard system may utilize these eye-tracking cameras to determine where a driver's attention is focused.

In some embodiments, the steering wheel may include one or more pressure sensors 106. These pressure sensors 106 may be configured to measure the amount of force being applied to the steering wheel. The onboard system may be configured to determine, using information collected from the one or more pressure sensors 106, that a user is distracted. For example, the onboard system may utilize one or more pressure sensor 106 to identify a baseline pressure for a particular user. Upon detecting an increase or decrease in pressure applied to the pressure sensors, the onboard system may determine that the driver is distracted (e.g., stressed out or focused on something other than driving). As depicted in FIG. 1C, a number of pressure sensors may be positioned so that pressure from various directions may be measured. For example, the pressure sensors 106 may be positioned along the exterior of the steering wheel in a radial fashion.

Although the one or more input sensors are depicted in FIG. 1 as being installed on the steering wheel, it should be noted that in some embodiments of the disclosure, the one or more input sensors may be located somewhere other than the steering wheel. Each of these embodiments is intended to be anticipated by the current disclosure. For example, the onboard system may include one or more sensors (e.g., accelerometers) capable of detecting sudden shifts in a vehicle's position. In this example, if the vehicles is determined to be moving from side to side (i.e., swerving), the onboard system may enable the distraction settings.

Figure 2:
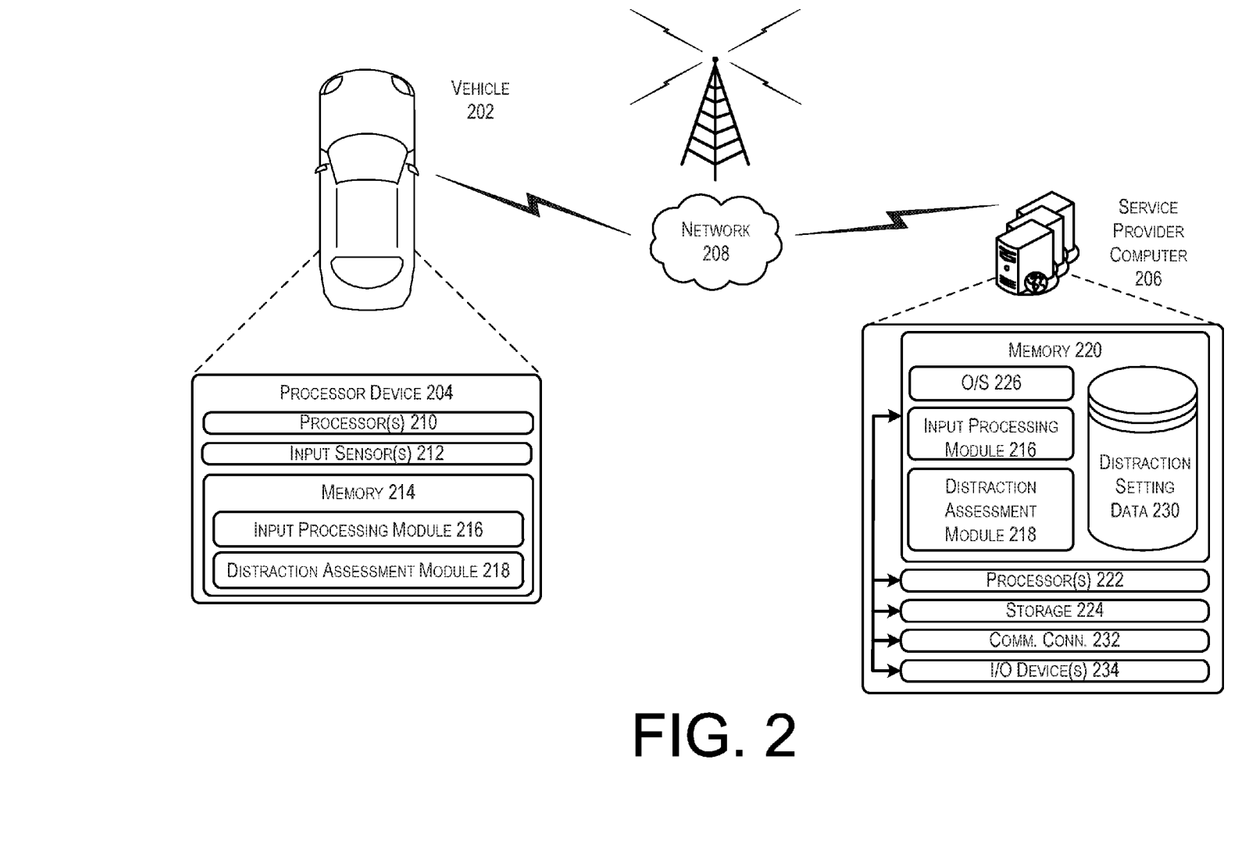
FIG. 2 depicts system or architecture in which techniques for determining a distraction level of a driver of a vehicle and implementing distraction settings may be implemented in accordance with the disclosure.

FIG. 2 depicts system or architecture in which techniques for determining a distraction level of a driver of a vehicle and implementing distraction settings may be implemented in accordance with the disclosure. In some examples, a vehicle 202 may include a processor device 204. In some embodiments, the processor device 204 may be configured to communicate with a service provider computer 206 via a network 208, or via other network connections. The processor device 204 or the service provider computer 206 may be configured to process an input received from one or more input sensors and provide instructions for implementing one or more distraction settings.

The processor device 204 may be any type of computing device capable of performing the described functions. The processor device 204 may include one or more processors 210 capable of processing input from one or more input sensors 212. As is known in the art, there are a variety of input sensors 212 capable of detecting input related to a user or vehicle conditions, such as pressure sensors, heart rate sensors, accelerometers, cameras, microphones, etc. The input obtained by the input sensors may be from a variety of data input types, including, but not limited to, audio data, visual data, or biometric data. Programmatic code for an application or module utilized in the implementation of at least some embodiments may be stored and executed from the memory 214 of processor device 204. The processor device 204 may include a module for processing input information related to a vehicle driver (input processing module 216) and/or a module for assessing a level of stress of the driver based on the processed input information (distraction assessment module 218).

In some examples, the network(s) 208 may include any one or a combination of many different types of networks, such as cable networks, the Internet, wireless networks, cellular networks, and other private and/or public networks. It is also noted that the described techniques may apply in other client/server arrangements, as well as in non-client/server arrangements (e.g., locally stored applications, peer to-peer systems, etc.). In an exemplary embodiment, the processor device 304 may communicate with a network hub using one or more wireless communication networks (e.g., 3G, 4G, etc.). The network hub may, in turn, utilize a physical connection (e.g., copper cable, T1, Ethernet, etc.) to communicate with the service provider computer at a network address.

The service provider computer 206 may be any type of computing device such as, but not limited to, a mobile phone, a smart phone, a personal digital assistant (PDA), a laptop computer, a desktop computer, a server computer, a thin-client device, a tablet PC, etc. Additionally, it should be noted that, in some embodiments, the service provider computer 206 may be executed by one or more virtual machines implemented in a hosted computing environment. The hosted computing environment may include one or more rapidly provisioned and released computing resources, which computing resources may include computing, networking, and/or storage devices. A hosted computing environment may also be referred to as a cloud-computing environment.

In one illustrative configuration, the service provider computer 206 may include at least one memory 220 and one or more processing units (or processor(s)) 222. The processor(s) 222 may be implemented as appropriate in hardware, computer-executable instructions, firmware or combinations thereof. Computer-executable instruction or firmware implementations of the processor(s) 222 may include computer-executable or machine executable instructions written in any suitable programming language to perform the various functions described.

The memory 220 may store program instructions that are loadable and executable on the processor(s) 210 and/or processor(s) 222, as well as data generated during the execution of these programs. Depending on the configuration and type of service provider computer 206, the memory 220 may be volatile (such as random access memory (RAM)) and/or non-volatile (such as read-only memory (ROM), flash memory, etc.). The service provider computer 206 may also include additional storage 224, such as either removable storage or non-removable storage including, but not limited to, magnetic storage, optical disks, and/or tape storage. The disk drives and their associated computer-readable media may provide non-volatile storage of computer-readable instructions, data structures, program modules, and other data for the computing devices. In some implementations, the memory 220 may include multiple different types of memory, such as static random access memory (SRAM), dynamic random access memory (DRAM) or ROM. Turning to the contents of the memory 220 in more detail, the memory 220 may include an operating system 226 and one or more application programs or services for implementing the features disclosed herein including at least a module for processing input information related to a driver (input processing module 216) and/or a module for assessing a driver's distraction level based on the processed input (distraction assessment module 218). The memory 220 may also include distraction setting data 230, which provides data related to identifying portions of image information. In some embodiments, the distraction setting data 230 may be stored in a database.

The memory 220 and the additional storage 224, both removable and non-removable, are examples of computer-readable storage media. For example, computer-readable storage media may include volatile or non-volatile, removable or non-removable media implemented in any method or technology for storage of information such as computer-readable instructions, data structures, program modules or other data. As used herein, modules may refer to programming modules executed by computing systems (e.g., processors) that are part of the processor device 204 or the service provider computer 206. The service provider computer 206 may also contain communications connection(s) 232 that allow the service provider computer 206 to communicate with a stored database, another computing device or server, user terminals, and/or other devices on the network(s) 208. The service provider computer 206 may also include input/output (I/O) device(s) and/or ports 234, such as for enabling connection with a keyboard, a mouse, a pen, a voice input device, a touch input device, a display, speakers, a printer, etc.

Turning to the contents of the memory 220 in more detail, the memory 220 may include an operating system 226, a database containing distraction setting data 230 and the one or more application programs or services for implementing the features disclosed herein, including an input processing module 216 and/or a distraction assessment module 218.

In some embodiments, the input processing module 216 may be configured to receive input information from one or more input sensors, process the input information, and provide the processed information to the distraction assessment module 218. In some embodiments, the input processing module may collect multiple input information from multiple different input sensors. In some embodiments, the input processing module 216 may compare the received input information to a baseline. For example, the driver may be associated with a baseline heart rate. In this example, heartrate information received from a heartrate sensor may be compared to the baseline heartrate. In some embodiments, the baseline may be comprised of an average of recent input information. For example, the baseline heartrate may be comprised of an average heartrate taken over the last three minutes. In this example, if the driver experiences a sudden elevation in his or her heart rate, then the input processing module may indicate the increased heart rate to the distraction assessment module 218. However, in this example, if the driver has had an elevated heart rate for a long period of time, then the driver's baseline heartrate would eventually rise and the input processing module 216 may indicate that the driver's heartrate is at the baseline.

In some embodiments, the distraction assessment module 218 may be configured to receive processed input information from the input processing module 216 and determine whether the driver is stressed out or otherwise distracted. In some embodiments, the distraction assessment module 218 may be configured to determine that a driver is stressed out if he or she is gripping the steering wheel too tightly. This may be determined by analyzing input information received from pressure sensors located in the steering wheel. In some embodiments, the distraction assessment module 218 may receive an indication that pressure is no longer being applied to at least a portion of the steering wheel. This may be an indication that the driver has removed his or her hand from the steering wheel at this location. In this example, the distraction assessment module 218 may determine whether pressure on other portions of the steering wheel has increased, which may indicate that the driver is leaning. If pressure on other parts of the steering wheel has not increased, then the distraction assessment module 218 may determine that the driver is driving with one hand. Alternatively, the distraction assessment module may determine that the driver is texting while driving. In some embodiments, the distraction assessment module may utilize a set of default rules. However, because this assessment may depend on the behavior habits of the particular driver, some embodiments may include the use of a personal distraction profile, as described below.

In some embodiments, the distraction setting data 230 at the service provider computer 206 may contain a distraction profile for one or more drivers. The distraction profile may include a list of indicators specific to that driver, as well as some default indicators. For example, the service provider computer 206 may provide a distraction profile that indicates Driver A has a habit of texting while driving. Additionally, the service provider computer 206 may provide a distraction profile that indicates Driver B never texts while driving. In applying the above scenario (in which the distraction assessment module 218 determined that the driver is driving with one hand) to each of the drivers, the distraction assessment module 218 may determine that Driver A is distracted while Driver B is not. In some embodiments, a driver's distraction profile may be provided to a vehicle on startup by a service provider computer 206. For example, upon identification of the driver, the service provider computer 206 may pre-load the driver's distraction profile into memory of the processor device 204. This allows a distraction assessment module 218 to be customized according to the driver. By way of illustrative example, consider a scenario in which a driver rents a vehicle from a vehicle rental agency. In this example, the driver may already have a distraction profile maintained by the rental agency. Once the rental agency creates a rental relationship between the driver and the rental vehicle, the driver's distraction profile may be uploaded to the rental vehicle.

Although described as being executed from the memory 220 of the service provider computer 206, the input processing module 216 and/or the distraction assessment module 218 may be located on, and executed from, the memory 214 of the processor device 204. In embodiments in which one or more of the modules are located on the service provider computer 206, the instructions for implementing one or more distraction settings may be transmitted to the vehicle and executed by the vehicle's onboard system.

Figure 3:
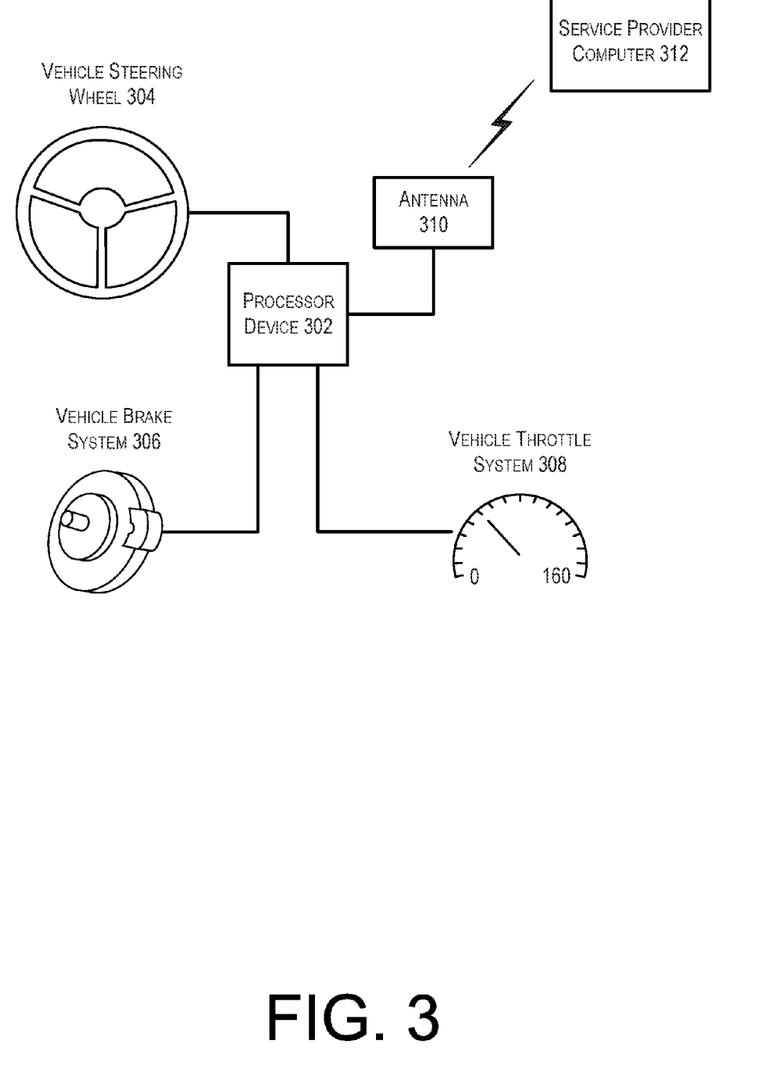
FIG. 3 depicts an illustrative example of the onboard system in accordance with at least some embodiments.

FIG. 3 depicts an illustrative example of the onboard system in accordance with at least some embodiments. In FIG. 3, a processor device 302 is depicted as being communicatively coupled to a vehicle's steering wheel 304, braking system 306, throttle system 308, and an antenna 310. The onboard system may include one or more component adjusters attached to the vehicle's braking system and/or the vehicle's throttle system. In the depicted illustrative example, the antenna 310 is in communication with a service provider computer 312. It should be noted that not all embodiments of the onboard system will include an antenna 310 and/or a service provider computer 312.

In the illustrative example, the processor device 302 may receive an indication that the driver is gripping the steering wheel very tightly. This indication may be received from one or more pressure sensors located within the steering wheel 304. Upon receiving this indication, the processor device may determine that the user is stressed out or angry (and therefore distracted). In the depicted example, if the grip force applied to the steering wheel is above a threshold value, then the processor device 302 may send a signal to a component adjuster attached to the vehicle brake system 306 to increase the sensitivity of the brake pedal. For example, the processor device 302 may send a signal to a component adjuster attached to the master cylinder of the vehicle's braking system to cause an increase in the hydraulic pressure of the vehicle braking system 306. This may result in the vehicle's brake system becoming more sensitive, in that a movement of the vehicle's brake pedal will result in a greater braking force than the movement would typically result in.

Additionally, as depicted in the example, if the grip force applied to the steering wheel is above a threshold value, then the processor device 302 may send a signal to a component adjuster attached to the vehicle throttle system 308 to decrease the sensitivity of the vehicle's gas pedal. This may result in the vehicle's throttle system becoming less sensitive, in that a movement of the vehicle's gas pedal will result in a smaller acceleration than the movement would typically result in.

In some embodiments, the processor device 302 may receive a communication from the service provider computer 312 via the antenna 310. In some embodiments, the communication may include a distraction profile. In some embodiments, the service provider computer may perform one or more of the processes of the disclosed onboard system. For example, the service provider computer 312 may receive input related to the driver from one or more sensors of the onboard system, and may subsequently determine whether to activate a distraction setting. In this example, the service provider, upon determining that the driver is distracted, may transmit a signal to the processor device 302 to cause it to activate one or more distraction setting. As indicated above, not every embodiment of the disclosure will utilize an antenna 310 and/or a service provider computer 312.

Although the illustrative example in FIG. 3 discusses adjusting the sensitivity of a vehicle braking system 306 and/or a vehicle throttle system 308, it should be noted that a number of actions may be performed to increase the safety of a driving experience. For example, a vehicle's ADAS system may be activated upon detecting that the driver is distracted. This may result in an electronic stability program (ESP) taking over control of the braking/steering functions. It is intended that this disclosure encompass the activation of any suitable precautionary measure as a result of determining that a driver is distracted.

Figure 4A:
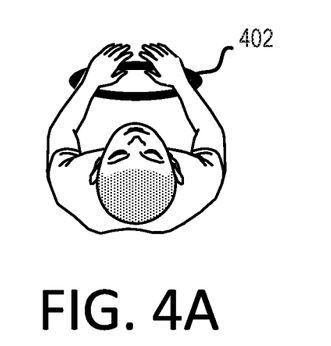
FIG. 4A depicts a first position for a driver in accordance with at least some embodiments.
Figure 4B:
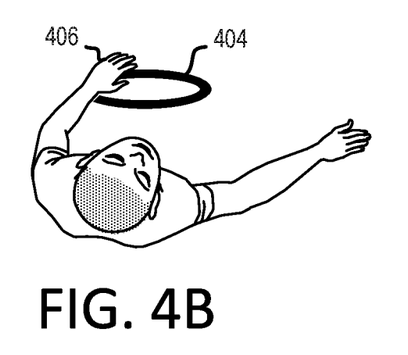
FIG. 4B depicts a second position for a driver in accordance with at least some embodiments.

FIG. 4 depicts an illustrative use case involving a driver in accordance with at least some embodiments. In FIG. 4, a driver is depicted in two separate positions along with a steering wheel 402. A first position for the driver is illustrated by FIG. 4A and a second position for the driver is illustrated by FIG. 4B. The first position illustrated in FIG. 4A represents an attentive or "normal" mode of vehicle operation for the driver. The second position illustrated in FIG. 4B represents a "distracted" mode of vehicle operation for the driver.

In FIG. 4A, a driver is depicted in a first position. In the depicted first position, the driver is attentive, having both hands on the steering wheel and looking forward. In this scenario, the onboard system may utilize pressure sensors located in the steering wheel 402 to determine that the both of the driver's hands are on the steering wheel 402 by detecting that grip force is being applied to the steering wheel 402 in at least two positions. Furthermore, the onboard system may determine that the grip force being applied to the steering wheel is below a threshold value and therefore indicates a normal level of stress. Under these conditions, the onboard system may determine that the driver is not stressed out nor distracted. The onboard system may implement regular driving settings under these conditions.

In FIG. 4B, the driver is depicted in a second position. In the depicted second position, the driver is distracted, having only one hand on the steering wheel and focused on something other than driving. The onboard system may utilize pressure sensors located in the steering wheel 402 to determine that only one of the driver's hands are on the steering wheel 402 by detecting that grip force is being applied to the steering wheel 402 in only one position. Additionally, the onboard system may determine that the driver is leaning or reaching upon detecting that the grip force applied by the one remaining hand is greater than it typically should be. Under these conditions, the onboard system may determine that the driver is distracted. The onboard system may subsequently implement one or more distraction settings under these conditions.

Figure 5:
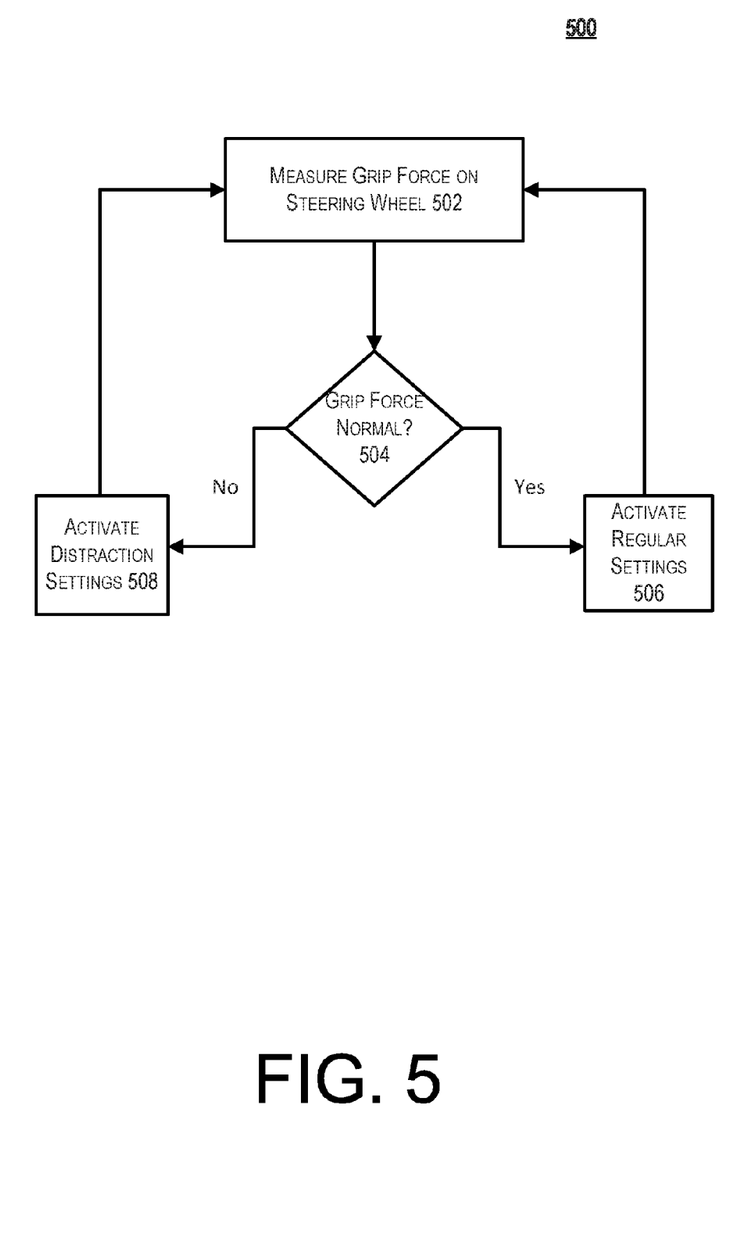
FIG. 5 depicts an illustrative flow chart demonstrating an example process that may be performed by the disclosed onboard system in accordance with at least some embodiments.

FIG. 5 depicts an illustrative flow chart demonstrating an example process that may be performed by the disclosed onboard system in accordance with at least some embodiments. The process 500 is illustrated as a logical flow diagram, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement this process and any other processes described herein.

Some or all of the process 500 (or any other processes described herein, or variations and/or combinations thereof) may be performed under the control of one or more computer systems configured with executable instructions and may be implemented as code (e.g., executable instructions, one or more computer programs or one or more applications). In accordance with at least one embodiment, the process 500 of FIG. 5 may be performed by at least the one or more processor devices 204 shown in FIG. 2. The code may be stored on a computer-readable storage medium, for example, in the form of a computer program including a plurality of instructions executable by one or more processors. The computer-readable storage medium may be non-transitory.

Process 500 depicts a process loop in that, once the process 500 has been entered, the process 500 may continually repeat until the loop is exited. In some embodiments, this process loop may be entered into upon a vehicle engine being started or a vehicle transmission being put into gear. In some embodiments, this process loop may be exited upon detecting that the vehicle's engine has been shut off or that the vehicle's transmission has been taken out of gear. Process 502 may begin at 502, when an onboard system measures the amount of grip force being applied to a steering wheel. In some embodiments, this may be done using one or more pressure sensors attached to the steering wheel.

Once the grip force has been measured, the process may determine whether the grip force is above a threshold or baseline value. In some embodiments, the baseline value may be preprogrammed (e.g., corresponding to a value stored in the memory of the onboard system). In some embodiments, the onboard system may measure an increase in grip force being applied to the steering wheel. For example, the onboard system may determine an average grip force applied to the steering wheel within an interval of time. The onboard system may then use this average grip force as a threshold or baseline value. Although the process 500 is described with respect to grip force applied to a steering wheel, it should be noted that the onboard system may determine a driver's level of distraction using other means. For example, the onboard system may measure the driver's heart rate using a heart rate sensor. In this example, the driver's heartrate may be compared to a threshold value.

In some embodiments, if the measured grip force is normal (e.g., below the threshold value or within an acceptable range), then the onboard system may apply regular driving settings as depicted at 506. If the grip force is abnormal (e.g., above the threshold value or outside of an acceptable range), then the onboard system may determine that the driver may be prone to driving erratically. Under these circumstances, the onboard system may apply at least one distraction setting, as depicted at 508. Once the appropriate driving setting has been applied, the process 500 may repeat, starting back at 502.

Figure 6:
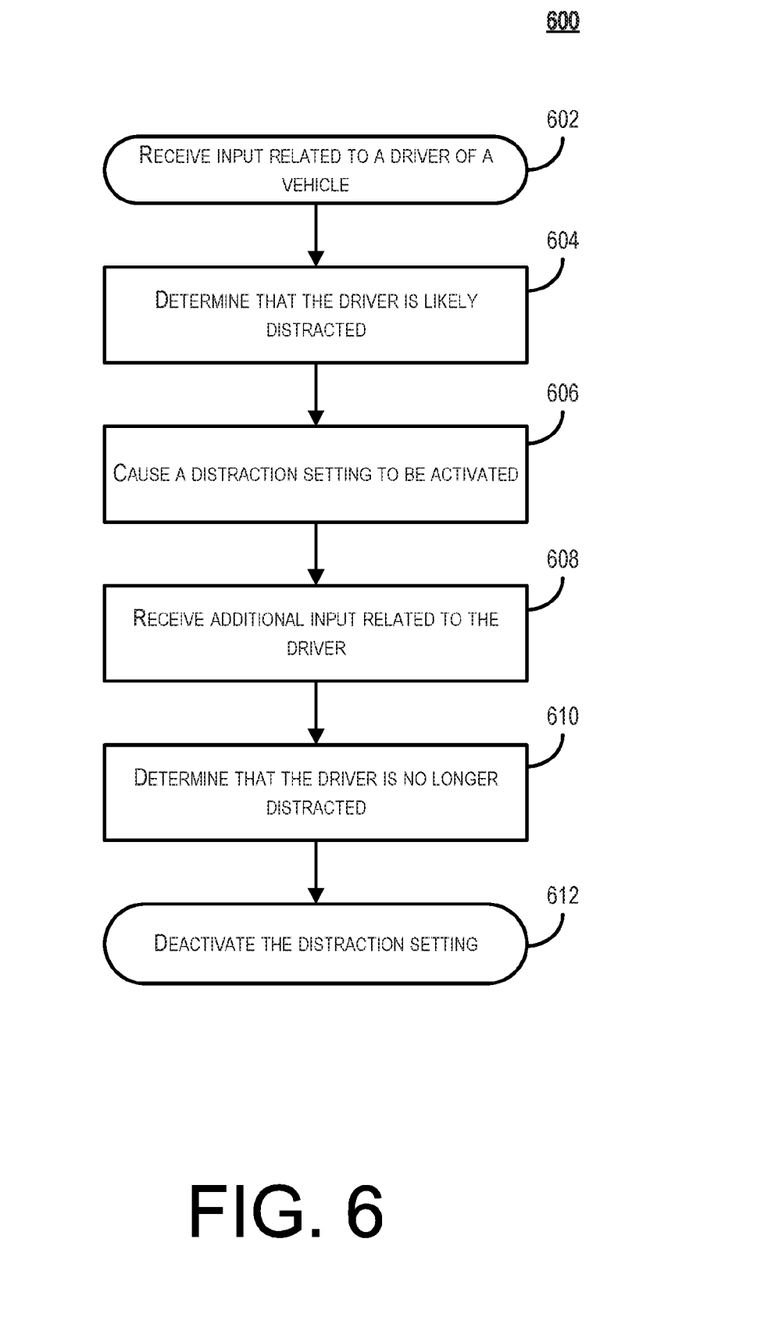
FIG. 6 depicts an illustrative flow diagram depicting an example process for detecting driver distraction and implementing distraction settings in accordance with at least some embodiments.

FIG. 6 depicts an illustrative flow diagram depicting an example process for detecting driver distraction and implementing distraction settings in accordance with at least some embodiments. In accordance with at least one embodiment, the process 600 of FIG. 6 may be performed by at least the one or more processor devices 204 shown in FIG. 2.

Process 600 of FIG. 6 may begin at 602, when a processor device receives input from one or more input sensors related to a driver of a vehicle in which the processor device is located. The input related to the driver may be analyzed to determine whether it is within acceptable bounds. In some embodiments, this may be done by determining whether the input received is within a threshold range stored at the processor device. It is envisioned that this threshold range may vary by driver. For example, in the case in which input is provided by pressure sensors on the steering wheel, one driver may use a different amount of grip force than another driver under normal driving conditions. Accordingly, in some embodiments, a distraction profile for a driver may include an indication of the amount of grip force typically used by that driver. The processor device may receive the distraction profile for a driver from the service provider computer prior to beginning process 600. In some embodiments, the threshold range may be calculated based on an average range of input over a time interval. For example, the processor device may measure the average grip force applied to the steering wheel over the last three minutes. The processor device may then apply a plus and minus value to identify an acceptable range of input.

Upon receiving input from the one or more input sensors, a processor device may determine, based on that received input, whether the driver is currently distracted at 604. In some embodiments, the processor device may determine that the received input is outside of the acceptable range of input values. In some embodiments, the processor device may determine that the driver is exhibiting a particular type of distraction based on received input. For example, the processor device may receive an indication that grip force has decreased on one side of the steering wheel and increased on the other side of the steering wheel. This may lead the processor device to determine that the driver is leaning to one side, or potentially reaching for something, and is therefor distracted.

Upon determining that a driver is currently distracted, the process 600 may cause a distraction setting to be activated at 606. The distraction settings may be applied based at least in part on what kind of driver distraction is detected. For example, if the driver is detected to be focusing on something other than driving, then the vehicle's ADAS system may be activated, resulting in an electronic stability program (ESP) taking over control of the braking/steering functions. In another example, if the driver is detected to be texting while driving, then audio warnings may be activated to alert the driver as to driving conditions.

In some embodiments, the process may continue to receive input associated with the driver. In some cases, the factors that originally caused the process 600 to determine that the driver is distracted may dissipate. In some cases, additional input may be received that indicates the driver is no longer distracted at 610. Upon receiving an indication that the factors used to determine that the driver was distracted have dissipated, or upon receiving additional input that indicates the driver is no longer distracted, the process 600 may deactivate the distraction setting at 612. In some embodiments the process may activate a set of default (or regular) settings.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

What is claimed is:

1. An onboard vehicle apparatus operatively connected to a service provider computer configured to store profiles of drivers, the on-board vehicle apparatus comprising:
    one or more input sensors;
    one or more component adjusters communicatively coupled to one or more components of a vehicle, wherein the one or more component adjusters include a brake force adjuster attached to a master cylinder of a braking system of the vehicle and a throttle adjuster attached to a throttle system of the vehicle; and
    a processor device configured to:
        receive a profile of a driver of the vehicle, wherein the profile of the driver includes indication information indicating the driver is distracted when a condition of the driver is detected;
        transmit the profile of the driver to a service provider computer for updating a corresponding profile of the driver stored at the service provider computer;
        receive input from the one or more input sensors, the input related to the condition of the driver;
        transmit the sensor input to the service provider computer via an on-board antenna for determining whether the driver is distracted based on the profile of the driver stored at the service provider computer;
        receive a determination from the service provider computer via the antenna that the driver is determined to be distracted based on the sensor input and the profile of the driver; and
        in response to receiving the determination by the service provider computer that the driver is distracted, send signals to the brake force adjuster and the throttle adjuster, the signals instructing the brake force adjuster to cause an increased brake sensitivity of the braking system by increasing a hydraulic pressure of the braking system of the vehicle and instructing the throttle adjuster to cause a decreased gas pedal sensitivity by decreasing an output of the throttle system.

2. The onboard vehicle apparatus of claim 1, wherein the indication information indicates that the driver is distracted if the driver is detected to use only one hand to control a steering wheel of the vehicle.

3. The onboard vehicle apparatus of claim 1, wherein the one or more input sensors is configured to capture input associated with an operator of the onboard vehicle apparatus.

4. The onboard vehicle apparatus of claim 3, wherein the one or more input sensors includes at least one of a pressure sensor, a heartrate sensor, a thermometer, a sweat sensor, a camera device configured to capture facial expressions, and eye-tracking cameras configured to track eye movements.

5. A method for detecting whether a driver of a vehicle is distracted, the method being implemented by a processor on-board the vehicle, the method comprising:
receive a profile of a driver of the vehicle, wherein the profile of the driver includes indication information indicating the driver is distracted when a condition of the driver is detected;
transmit the profile of the driver to a service provider computer for updating a corresponding profile of the driver stored at the service provider computer;
receiving, from one or more input sensors, input related to a driver of a vehicle;
transmit the sensor input to the service provider computer via an on-board antenna for determining whether the driver is distracted based on the profile of the driver stored at the service provider computer;
receiving a determination from the service provider computer via the antenna that the driver is determined to be distracted based on the sensor input and the profile of the driver;
in response to receiving the determination that the driver is likely distracted, send signals to a brake force adjuster and a throttle adjustor of the vehicle, the signals instructing the brake force adjuster to cause an increased brake sensitivity of a braking system of the vehicle by increasing a hydraulic pressure of the braking system and instructing the throttle adjustor to cause a decreased gas pedal sensitivity by decreasing an output of a throttle system of the vehicle.

6. The method of claim 5, further comprising:
receiving additional input related to the driver;
determining, based at least in part on the additional input, that the driver is no longer distracted; and
in response to determining that the driver is no longer distracted, send a signal to the brake force adjuster to resume a normal brake sensitivity of the brake system.

7. The method of claim 5, wherein the one or more input sensors includes at least a heart rate sensor.

8. The method of claim 5, wherein the one or more input sensors includes at least a pressure sensor mounted on a steering wheel of the vehicle.

9. The method of claim 5, wherein the determination that the driver is distracted is made based on the input related to the driver exceeding a threshold value.

10. The method of claim 5, further comprising identifying a distraction profile associated with the driver of the vehicle, wherein the determination that the driver is likely distracted is made based at least in part on the distraction profile.

11. A vehicle onboard system, comprising:
one or more input sensors;
a processor device; and
a memory including instructions that, when executed with the processor device, cause the system to, at least:
receive a profile of a driver of a vehicle, wherein the profile of the driver includes indication information indicating the driver is distracted when a condition of the driver is detected;
transmit the profile of the driver to a service provider computer for updating a corresponding profile of the driver stored at the service provider computer;
capture, via the one or more input sensors, input information related to the condition of the driver;
transmit the sensor input to the service provider computer via an on-board antenna for determining whether the driver is distracted based on the profile of the driver stored at the service provider computer;
receive a determination from the service provider computer via the antenna that the driver is determined to be distracted based on the sensor input including values outside of an acceptable range as indicated by the profile of the driver; and
in response to the determination that the driver is exhibiting distracted driving behavior, send signals to a brake force adjuster and a throttle adjuster of the vehicle, the signals instructing the brake force adjuster to cause an increased brake sensitivity of the braking system by increasing a hydraulic pressure of the braking system of the vehicle and instructing the throttle adjuster of the vehicle to cause a decreased gas pedal sensitivity by decreasing an output of a throttle system of the vehicle.

12. The vehicle onboard system of claim 11, wherein the acceptable range is specific to the driver.

13. The vehicle onboard system of claim 12, wherein the acceptable range is provided to the processor device by a service provider computer.

14. The vehicle onboard system of claim 11, wherein the acceptable range is calculated from an average input collected over a period of time.

* * * * *